United States Patent [19]

Hänsel et al.

[11] Patent Number: 4,584,394

[45] Date of Patent: Apr. 22, 1986

[54] ALKENYLBENZOYLOXYSILANES AND THEIR USE IN PRESSURE-SENSITIVE ADHESIVES

[75] Inventors: Edward Hänsel, Hochdahl; Hans Huber, Lohmar; Gerhard Geier, Lohmar-Geber; Claus Seiler, Rheinfelden, all of Fed. Rep. of Germany

[73] Assignee: Dynamit Nobel AG, Troisdorf, Fed. Rep. of Germany

[21] Appl. No.: 682,431

[22] Filed: Dec. 17, 1984

[30] Foreign Application Priority Data

Dec. 24, 1983 [DE] Fed. Rep. of Germany ....... 3346909

[51] Int. Cl.$^4$ ............................ C07F 7/04; C07F 7/08; C07F 7/18
[52] U.S. Cl. .................................................. 556/442
[58] Field of Search ......................................... 556/442

[56] References Cited

U.S. PATENT DOCUMENTS 2,397,287 3/1946 Ostberg ............................... 556/442

Primary Examiner—Paul F. Shaver
Attorney, Agent, or Firm—Felfe & Lynch

[57] ABSTRACT

New alkenylacyloxysilanes in which the acyloxy grouping is derived from benzoic acid and a method for making the new compounds are disclosed. The present invention also relates to the use of these new alkenylacyloxysilanes in making pressure-sensitive adhesives which are prepared by copolymerizing these new compounds with at least two other ethylenically unsaturated compounds. The crosslinking of these new pressure-sensitive adhesives is performed preferably with the aid of known crosslinking catalysts and/or by high-energy radiation.

9 Claims, No Drawings

ALKENYLBENZOYLOXYSILANES AND THEIR USE IN PRESSURE-SENSITIVE ADHESIVES

BACKGROUND OF THE INVENTION

The subject matter of the invention is new alkenylacyloxysilanes, a method for producing them, and their use in pressure-sensitive adhesives.

It is known to use vinylalkoxysilanes as comonomers in the preparation of copolymers from ethylenically unsaturated monomers. Furthermore, pressure-sensitive adhesives are known which are prepared by the copolymerization of N-vinyl lactams and acrylic acid esters (German Publication DE-PS No. 19 64 743). The crosslinking of these pressure-sensitive adhesives is accomplished either by radiation or by means of organic peroxides.

U.S. Pat. No. 3,971,751 furthermore discloses adhesives made from polyethers having terminal silyl ether groups. In their crosslinking, the hydrolyzable groups (e.g., alkoxy groups) on the silyl terminal groups hydrolyze to form an Si-O-Si bond.

It has already been proposed to make use of the hydrolyzability of alkoxysilyl groups for crosslinking in pressure-sensitive adhesives on the basis of copolymers having ethylenically unsaturated groups (German Patent Application P No. 32 32 923.7), but only vinylalkoxysilanes are used as comonomers, whose alkoxy groups often hydrolyze but very slowly in the copolymers. Also, in the above-named adhesives having silyl ether terminal groups, the hydrolysis often takes so long, due to the alkoxy terminal groups, that pressure-sensitive systems which crosslink by hydrolysis of alkoxysilyl terminal groups involve disadvantages on account of the slowness of the hydrolysis.

The problem therefore existed of finding solvent-free pressure-sensitive adhesive systems which are based on copolymers of ethylenically unsaturated compounds, crosslink relatively rapidly, and form physiologically unobjectional and noncorrosive hydrolysis products.

THE INVENTION

For the solution of this problem, alkenylacyloxysilanes have been found having the formula

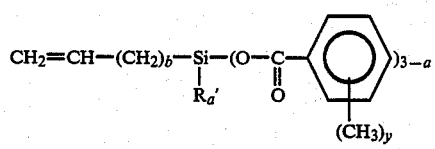

wherein R' can represent identical or different moieties from the group of alkyls of 1 to 4 carbon atoms and alkoxies of 1 to 4 carbon atoms, a can be equal to 0 or 1 or 2, y can be equal to 0 or 1 and b can be equal to 0 or 1, which can be used as comonomers in pressure-sensitive adhesives on a basis of copolymers of at least two ethylenically unsaturated compounds.

Olefinically unsaturated hydrolyzable silanes having acyl functions are already known; in these silanes, however, the acyl function derives from aliphatic carboxylic acids (Ostberg, U.S. Pat. No. 2,397,287). In their hydrolysis, acetic acid is formed, which has the disadvantage that sometimes it is corrosive and has properties which are physiologically objectionable. Acyl moieties of higher aliphatic carboxylic acids produce in their hydrolysis cleavage products which have an intensely unpleasant odor, so that compounds containing these moieties are not suitable for the desired purpose.

The preparation of the new compounds can be performed in a known manner by the reaction of alkenyl halogen silanes with benzoic acid. The alkenyl halogen silanes that can be used as starting products can be substituted at the silicon atom by one or two alkyl moieties, and these moieties can have up to 4 carbon atoms. The chlorine compound is the preferred halogen compound.

Depending on the selection of the starting product, the following are obtainable in this manner: vinyl-tribenzoyloxysilane, allyl-tris-benzoyloxysilane, vinylmethyldibenzoyloxysilane, vinylethyldibenzoyloxysilane, vinyldimethylbenzoyloxysilane, allylmethyldibenzoyloxysilane, allyldimethylbenzoyloxysilane, vinylbutyldibenzoyloxysilane, and the corresponding compounds substituted by a methyl group in the benzene nucleus.

The new compounds, however, can also be prepared from alkenylalkoxysilanes by reaction with benzoic acid anhydride. For each alkoxy group that is to be split off, one mole of benzoic acid anhydride is used. If only one alkoxy group is to be split off, the vinyl silane is best used in an excess. The reaction takes place at elevated temperature, generally between 120° and 150° C., depending on the vinyl silane used. After the reaction has taken place, the benzoic acid ester that has formed, as well as any excess alkenylalkoxysilane, are distilled off, and then the desired acyloxysilane is obtained by fractional distillation.

In this manner, especially those alkenylsilanes can be prepared which contain both acyloxy and alkoxy groups, examples being vinylbenzoyloxydimethoxysilane, vinyldibenzoyloxymethoxysilane, or vinylbenzoyloxydiethoxysilane.

With the new alkenylacyloxysilanes, new copolymers can be prepared which can be used as pressure-sensitive adhesives. Suitable additional monomeric components of these copolymers are olefinically unsaturated compounds such as vinyl esters of higher fatty acids, vinyl lactams and acrylic or methacrylic acid ester. The ester component of the acrylic acid ester can have 4 to 24 carbon atoms; preferably, however, it contains 4 to 12 carbon atoms. The higher fatty acids of the vinyl ester component will be those having 12 or more carbon atoms, vinyl laurate being an example.

The olefinically unsaturated monomers are used in the new copolymers preferably in the form of mixtures, in which the content of the acrylic and methacrylic acid esters can be 50 to 80% by weight, that of the vinyl lactams or of N-vinylmethylacetamide 5 to 30% by weight, and that of styrene 5 to 25% by weight.

The preparation of such new copolymers is performed in a manner known in itself, by radical polymerization of the polymers cited. The molecular weights of the copolymers thus obtained are to be between 10,000 and 300,000, preferably between 50,000 and 100,000. If molecular weights under 100,000 are desired, polymerization regulators, such as aliphatic mercaptans, for example, can be added to the mixture.

Suitable polymerization initiators are, for example, organic peroxides such as benzoyl peroxide or cumene hydroperoxide, azo compounds such as azo-bis-isobutyronitrile, azo-bis-valeronitrile or also ammonium peroxide. The amount of initiator is around 0.05 to 0.9% of the weight of the solid content of the copolymers.

The polymerization can be performed either with or without solvent. The use of solvent is especially preferred if products of low molecular weight are to be obtained, which can then be applied to the substrate immediately as pressure-sensitive adhesives, after the admixture, in some cases, of a crosslinking catalyst.

If the polymerization is to be performed as a solvent polymerization, it is preferred to use as solvents those compounds which are capable of dissolving the monomers and especially the polymers. Such solvents are known to the person skilled in the art. Examples are acetic acid alkyl esters and aromatic hydrocarbons which are fluid at room temperature, as well as dioxane or methyl isobutyl ketone.

After the copolymerization has been performed, any solvent that is used is largely distilled out; the copolymers then obtained are stable when stored at room temperature with the exclusion of moisture. Temperatures over 40° C. over a period of several hours should be avoided in storage.

The new copolymers crosslink at a satisfactory rate at room temperature with atmospheric moisture, even without the addition of accelerators. However, it is also possible to accelerate the crosslinking by means of known crosslinking catalysts. The latter are used in amounts between 0.03 and 2.0, preferably between 0.1 and 1.0% by weight, with respect to the pressure-sensitive adhesive. They are added preferably before the adhesive is applied to the substrate.

Suitable crosslinking catalysts are, for example, organic tin compounds, such as dioctyltin diacetate, dibutyltin dilaurate, dibutyltin maleate, organic sulfonic acids such as p-toluenesulfonic acid, dodecylbenzenesulfonic acid or aqueous solutions (approx. 50 to 65% solutions) of hypophosphorous acid.

The uncrosslinked pressure-sensitive adhesive is applied to the support material in a thin coat, at slightly elevated temperature if desired, but below 80° C. as a rule; the coating between 15 and 50 microns.

For the further acceleration of the crosslinking, the uncrosslinked pressure-sensitive adhesive can be irradiated after application with infrared radiation of 2 to 5 micrometers wavelength. Depending on the formula, the time of irradiation is between 12 and 120 seconds.

EXAMPLES

EXAMPLE 1

Preparation of vinyltribenzoyloxysilane

A six-liter three-necked flask is placed in a mushroom heating hood, and equipped with a stirrer, a reflux condenser and a dropping funnel whose nozzle bore amounts to 1 cm. 808 g (5 moles) of vinyltrichlorosilane and 1000 ml of hexane are introduced into the flask. The outlet from the reflux condenser is shielded with nitrogen. After the liquid has been heated until an intensive refluxing is taking place at the condenser, 1855 g (15.2 mol) of benzoic acid is added in 30-gram portions. The addition is completed in about 20 hours. The reaction is allowed to run, with refluxing and vigorous stirring, until the analytically determined contents of hydrolyzable chlorine amount to less than 100 parts per million.

The raw product thus obtained is transferred to a distillation apparatus. The solvent is removed, first at standard pressure, and when a bottom temperature of 120° C. is reached, the solvent is removed with the application of a vacuum. After an intermediate run, at 0.5 mbar and a top temperature of 141° C., 1651 g (3.95 mol) of a liquid is distilled out, which gradually passes over into an oily-crystalline state. The yield amounts to 79%.

The elemental analysis of the product is represented as follows:

|  | C | H | Si | Molecular weight |
|---|---|---|---|---|
| Calculated: | 66% | 4.3% | 6.7% | 418 |
| Found: | 66.3% | 4.2% | 6.9% | 420 |
| Boiling point: | 141° C./0.5 mbar | | | |
| Melting point: | 35° C. | | | |
| $d_{25}^{25}$: | 1.18 g/cm$^9$ | | | |

EXAMPLE 2

Preparation of vinylmethyldibenzoyloxysilane 705 g (5 moles) of vinylmethyldichlorosilane and 1000 ml of hexane are placed in the apparatus of Example 1. The reaction with 1245 g of benzoic acid (=10.2 moles) is performed as described under Example 1; the distillation of the raw product is performed in the same manner. At a pressure of 0.5 mbar and a head temperature of 141° C., 1295 g (4.15 moles) of a colorless liquid is distilled off. The yield amounts to 83%.

The elemental analysis of the product is as follows:

|  | C | H | Si | Molecular weight |
|---|---|---|---|---|
| Calculated | 65.4% | 5.1% | 9% | 312 |
| Found | 65.1% | 5.2% | 8.8% | 317 |
| Boiling point: | 141° C./0.5 mbar | | | |
| $d_{25}^{25}$: | 1.146 | | | |

EXAMPLE 3

Preparation of Allyltribenzoyloxysilane 878 g (5 moles) of allyltrichlorosilane and 1000 ml of hexane are placed in the apparatus of Example 1. The reaction with 1855 g of benzoic acid (=15.2 mol) is performed as described in Example 1, as is also the distilling of the raw product. At a pressure of 0.4 mbar and a head temperature of 137° C., 1599 g (3.7 mol) of a colorless liquid is distilled out, which several days later transforms to a sticky-crystalline state. The yield of 74%.

The elemental analysis of the product is as follows:

|  | C | H | Si | Molecular weight |
|---|---|---|---|---|
| Calculated: | 66.7% | 4.6% | 6.5% | 432 |
| Found: | 66.4% | 4.7% | 6.3% | 425 |
| Boiling point: | 137° C./0.4 mbar | | | |

EXAMPLE 4

Preparation of vinylbenzoyloxydimethoxysilane 2370 g (16 mol) of vinyltrimethoxysilane, 2262 g (10 mol) of benzoic acid anhydride and 2 g of toluenesulfonic acid are placed in the apparatus of Example 1.

The mixture is heated at about 130° C. and let stand at this temperature for 40 hours. After this period of time the reaction product is tested by gas chromatography for the presence of benzoic acid anhydride. No more of the latter could be detected.

The reaction product is then transferred to a distillation apparatus and vacuum distilled. After removal of the excess vinyl trimethoxysilane and of the benzoic acid methyl ester that has formed, 1309 g (5.5 mol) of a colorless liquid is distilled out at 1.5 mbar and a head temperature of 55° C. The yield, with respect to benzoic acid anhydride, amounts to 55%.

The elemental analysis of the product is as follows:

|  | C | H | Si | Molecular weight |
|---|---|---|---|---|
| Calculated: | 55.5% | 5.9% | 11.8% | 238 |
| Found: | 55.7% | 6.1% | 11.6% | 244 |
| Boiling point: | 55° C./1.5 mbar | | | |

PREPARATION OF THE COPOLYMERS

EXAMPLE 5

A 1000-milliliter three-necked flask with stirrer, superimposed reflux condenser and nitrogen gas flooding serves as the reaction vessel. The following are placed in the flask: 270 g of ethylhexylacrylate, 80 g of styrene, 40 g of N-vinylpyrrolidone and 10 g of vinyl dimethoxymonobenzoyloxysilane as well as 400 ml of anhydrous ethyl acetate. 2.0 g of benzoyl peroxide is added to the mixture as the final component. Polymerization is performed at 80° C. with gentle refluxing for 24 hours; then the solvent is withdrawn by the vacuum of a water-jet pump, and a very viscous polymeric product which still pours at room temperature. It is stored with the exclusion of moisture.

EXAMPLE 6

The procedure of Example 5 was repeated except that, instead of vinyl dimethoxymonobenzoyloxysilane, 10 g of vinyl dibenzoyloxymonomethoxysilane was used. After 24 hours of reaction, when the solvent was withdrawn, the product was a transparent oil that was viscous at room temperature.

EXAMPLE 7

By the procedure of Example 5, 220 g of ethylhexylacrylate, 40 g of styrene, 30 g of N-vinylmethylacetamide and 10 g of vinyldimethoxymonobenzoyloxysilane were polymerized with 1.5 g of benzoylperoxide as catalyst. 300 ml of ethyl acetate was used as solvent. The polymerization time was 24 hours. After withdrawal of the solvent, there remained a thick liquid polymer which could still be poured at room temperature.

EXAMPLE 8

By the procedure of Example 5, 140 g of ethylhexyl acrylate, 20 g of N-vinylmethylacetamide, 30 g of styrene and 10 g of vinyl tribenzoyloxysilane were polymerized. 150 ml of anhydrous toluene served as solvent, and 1.0 g of benzoyl peroxide was used as catalyst. Polymerization was performed for 24 hours at 80° C. After withdrawal of the solvent, a transparent, thick liquid polymer was obtained.

EXAMPLE 9

In the apparatus described in Example 5, the following were dissolved in 85 ml of anhydrous ethyl acetate: 135 g of ethylhexylacrylate, 43.65 g of styrene, 20 g of N-vinylpyrrolidone and 1.4 g of vinyldimethoxymonobenzoyloxysilane. The catalyst was 0.6 g of benzoyl peroxide; the polymerization time was 24 hours at 80° C. After withdrawal of the solvent by the vacuum of a water-jet pump, a very thick liquid, transparent polymer results, having a molecular weight $\overline{M}$ of 260,000.

EXAMPLE 10

Polymerization using a regulator

In an apparatus like that described in Example 5, the following were polymerized: 135 g of ethylhexyl acrylate, 40 g of styrene, 20 g of N-vinylpyrrolidone and 5 g of vinyldimethoxymonobenzoylsilane in 200 ml of anhydrous ethyl acetate. The catalyst was 1.0 g of benzoyl peroxide, and the temperature was 80° C. After 4.5 hours the polymerization was stopped by adding 4.0 g of dodecyl mercaptan. The solvent was withdrawn in a low vacuum. A transparent, colorless, fluid polymer was obtained having a molecular weight $\overline{M}$ of 112,000.

EXAMPLE OF A PRESSURE-SENSITIVE ADHESIVE

General

The copolymer described in Example 9 was treated with 0.5 weight-percent, with reference to the total mass, of dodecylbenzenesulfonic acid as crosslinking catalyst, and homogenized.

The pressure-sensitive adhesive preparation thus obtained was applied uncrosslinked by means of a print coater, at temperatures of 70° C., to a polyester film 36 micrometers thick. The thickness of the coating was likewise 36 micrometers. Then the coating was irradiated with infrared light for 45 seconds and then protected with silicone paper. After about 30 minutes it was tested by the following methods.

Test Methods (a) Resistance to Peeling

An adhesive strip coated as described above, measuring 50×25 mm, is laid on a dust-free, degreased and dry piece of sheet steel and pressed with with a 2-kilogram hard rubber roller. The plate is suspended vertically and let stand for 10 minutes at 23° C. and 60% atmospheric humidity; then the sample is loaded with 500 g at an angle of 180° and the time is measured that it takes to peel off the 50 mm of the strip.

(b) Resistance in Shear

A piece of film coated with pressure-sensitive adhesive and measuring 25×25 mm is adhered to a dry, clean, greasefree piece of sheet iron and pressed down with a 2-kilogram hard rubber roller without bearing down on it. After 10 minutes of standing, the film is loaded with a 1000 g weight, and the time it takes for the weight to fall off is measured.

After this very brief span of time, the resistance to peeling was 5 minutes and the resistance in shear was 4 minutes.

It will be understood that the specification and examples are illustrative but not limitative of the present invention and that other embodiments within the spirit and scope of the invention will suggest themselves to those skilled in the art.

We claim:

1. An alkenylaceloxysilane of the formula

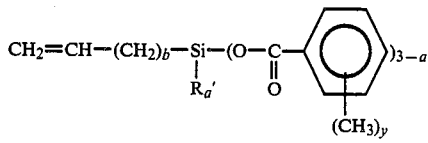

in which R' can represent identical or different moieties from the group $C_{1-4}$-alkyl or $C_{1-4}$-alkoxy, b=0 or 1, y=0 or 1 and a can be equal to 0 or 1 or 2.

2. The alkenylacyloxysilane of claim 1 designated as vinyltribenzoyloxysilane.

3. The alkenylacyloxysilane of claim 1 designated as vinylmethyldibenzoyloxysilane.

4. The alkenylacyloxysilane of claim 1 designated as allyltribenzoyloxysilane.

5. The alkenylacyloxysilane of claim 1 designated as vinylbenzoyloxydimethoxysilane.

6. A method for the preparation of an alkenylacyloxysilane of claim 1, comprising reacting an alkenylalkoxysilane with benzoic acid anhydride.

7. The method of claim 6, wherein the benzoic acid anhydride is substituted in the nucleus by methyl.

8. The method of claim 6, wherein the alkenylalkoxysilane is a vinyl or allylalkoxysilane.

9. The method of claim 6, wherein the alkenylalkoxysilane contains one or more alkoxy groups of 1 to 4 carbon atoms.

* * * * *